United States Patent
Otsuki et al.

(10) Patent No.: US 10,450,439 B2
(45) Date of Patent: Oct. 22, 2019

(54) RUBBER-METAL ADHESION PROMOTER, RUBBER COMPOSITION, AND TIRE

(71) Applicants: DIC Corporation, Tokyo (JP); National University Corporation, Iwate University, Morioka-shi (JP)

(72) Inventors: Shujiro Otsuki, Ichihara (JP); Takayuki Odashima, Ichihara (JP); Hidetoshi Hirahara, Morioka (JP)

(73) Assignees: DIC Corporation, Tokyo (JP); National University Corporation, Iwate University, Morioka-shi (JP)

( * ) Notice: Subject to any disclaimer, the term of this patent is extended or adjusted under 35 U.S.C. 154(b) by 308 days.

(21) Appl. No.: 15/507,834

(22) PCT Filed: Sep. 9, 2015

(86) PCT No.: PCT/JP2015/075596
§ 371 (c)(1),
(2) Date: Mar. 1, 2017

(87) PCT Pub. No.: WO2016/039376
PCT Pub. Date: Mar. 17, 2016

(65) Prior Publication Data
US 2017/0260357 A1    Sep. 14, 2017

(30) Foreign Application Priority Data

Sep. 12, 2014 (JP) ................................ 2014-187061

(51) Int. Cl.
| | |
|---|---|
| C08K 5/098 | (2006.01) |
| B60C 1/00 | (2006.01) |
| C08K 5/52 | (2006.01) |
| C08K 5/55 | (2006.01) |
| C08L 21/00 | (2006.01) |
| B60C 9/00 | (2006.01) |
| C07C 53/128 | (2006.01) |

(52) U.S. Cl.
CPC ............... C08K 5/098 (2013.01); B60C 1/00 (2013.01); B60C 9/0007 (2013.01); C07C 53/128 (2013.01); C08K 5/52 (2013.01); C08K 5/55 (2013.01); C08L 21/00 (2013.01)

(58) Field of Classification Search
CPC .................................................. C08K 5/098
See application file for complete search history.

(56) References Cited

U.S. PATENT DOCUMENTS

| | | | |
|---|---|---|---|
| 3,296,242 A | 1/1967 | Turner et al. | |
| 3,467,683 A | 9/1969 | Harson et al. | |
| 4,234,496 A | 11/1980 | Harson | |
| 4,609,499 A | 9/1986 | Esashi et al. | |
| 5,098,946 A | 3/1992 | Kawazura et al. | |
| 6,353,047 B1 | 3/2002 | Hilton et al. | |
| 2016/0102415 A1* | 4/2016 | Sebe | B05D 3/102 428/412 |
| 2017/0253722 A1* | 9/2017 | Otsuki | B60C 1/00 |

FOREIGN PATENT DOCUMENTS

| | | |
|---|---|---|
| EP | 0466448 A1 | 1/1992 |
| JP | 49-039187 B1 | 10/1974 |
| JP | 55-017371 A | 2/1980 |
| JP | 60-109591 A | 6/1985 |
| JP | 60-158230 A | 8/1985 |

(Continued)

OTHER PUBLICATIONS

International Search Report dated Dec. 22, 2015, issued for PCT/JP2015/075596 and English translation thereof.

(Continued)

*Primary Examiner* — Megan McCulley
(74) *Attorney, Agent, or Firm* — Locke Lord LLP; James E. Armstrong, IV; Nicholas J. DiCeglie, Jr.

(57) ABSTRACT

A rubber-metal adhesion promoter characterized by including a compound (1) represented by the following general formula (A): (in the formula, Z represents a structure selected from the following formulae (z-1) to (z-4); M represents titanium or zirconium; and (RCOO) represents a residue of an aliphatic carboxylic acid having 2 to 25 carbon atoms)

[Chemical Formula 1]

$$[(RCOO)_3MO]_3Z \qquad (A)$$

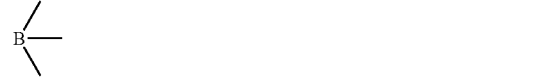

(z-1)

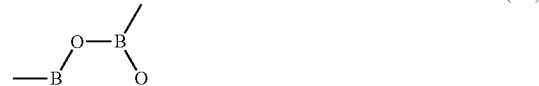

(z-2)

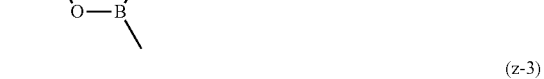

(z-3)

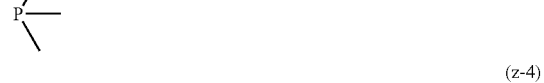

(z-4)

16 Claims, No Drawings

(56) References Cited

FOREIGN PATENT DOCUMENTS

| JP | 62-283987 A | 12/1987 |
| JP | 03-192130 A | 8/1991 |
| JP | 04-230397 A | 8/1992 |
| JP | 06-329839 A | 11/1994 |
| JP | 07-011052 A | 1/1995 |
| JP | 07-109478 A | 4/1995 |
| JP | 2006-160826 A | 6/2006 |
| WO | 2010/031745 A1 | 3/2010 |

OTHER PUBLICATIONS

Search Report dated Apr. 5, 2018, issued for the European patent application No. 15840758.5.

Li Xiao-ru et al., "Preparation and properties of nickel borate acylate", The Chinese Journal of Nonferrous Metals, vol. 11 No. 1, Feb. 2001. pp. 140-143 (English abstract is included. Cited in the Jan. 8, 2018 CN OA).

Office Action dated Jan. 8, 2018, issued for the Chinese patent application No. 201580048180.3 and partial English translation of the Search Report.

\* cited by examiner

RUBBER-METAL ADHESION PROMOTER, RUBBER COMPOSITION, AND TIRE

CROSS REFERENCE TO RELATED APPLICATIONS

This application is related to co-pending application: "RUBBER-METAL ADHESION PROMOTER, RUBBER COMPOSITION, AND TIRE" filed even date herewith in the names of Shujiro OTSUKI, Takayuki ODASHIMA and Hidetoshi HIRAHARA as a national phase entry of PCT/JP2015/075592, which application is assigned to the assignee of the present application and is incorporated by reference herein.

TECHNICAL FIELD

The present invention relates to a rubber-metal adhesion promoter, and a rubber composition and a tire using the same. More specifically, the present invention relates to an adhesion promoter capable of exerting a high adhesive force between rubber and a metal, which is equivalent to or higher than that of a cobalt-containing adhesion promoter, without containing cobalt associated with concerns over toxicity; and a rubber composition and a tire using the same.

BACKGROUND ART

Conventionally, in order to enhance the performance of automobile tires, belt conveyors and the like, for example, a steel cord or the like that is plated with brass has been used as a reinforcing material. In order to improve the adhesive force between the reinforcing material and natural rubber or synthetic rubber, the rubber contains an adhesion promoter. As the adhesion promoter, an organic acid cobalt metal soap (for example, cobalt stearate, cobalt naphthenate, cobalt tallate, cobalt boron metal soap, or the like) has been frequently used because of favorable adhesive properties with the steel cord and the rubber.

However, cobalt compounds such as the aforementioned organic acid cobalt metal soaps are listed in Group 2B which is said to be "possibly carcinogenic to humans" in the list of carcinogenic risks classified by the International Agency for Research on Cancer. In addition, since metallic cobalt which is a raw material of various cobalt compounds is a rare metal, its supply is unstable. As described above, cobalt compounds (organic acid cobalt metal soaps) using a raw material which is suspected to be carcinogenic and also unstable in supply tend to be avoided although the adhesive properties with rubber and the metal (steel cord) are favorable, and there is a demand for alternative adhesion promoters (non-cobalt based adhesion promoters).

As a non-cobalt based adhesion promoter, for example, an adhesion promoter containing boron or phosphorus has been known. More specifically, for example, an adhesion promoter having a structure containing three atoms of nickel or bismuth bonded to boron or phosphorus via an oxygen atom and having both a residue of an aromatic carboxylic acid and a residue of an aliphatic carboxylic acid has been known (for example, see Patent Document 1). However, the adhesion promoter disclosed in Patent Document 1 has a problem in that the adhesive force when adhering the rubber and the metal is not sufficient.

CITATION LIST

Patent Document

[Patent Document 1] Japanese Unexamined Patent Application, First Publication No. Hei 4-230397

SUMMARY OF INVENTION

Technical Problem

The problem to be solved by the present invention is to provide an adhesion promoter capable of exerting a high adhesive force between rubber and a metal than a cobalt-containing adhesion promoter without containing cobalt which is associated with concerns over toxicity; and a rubber composition and a tire using the same.

Solution to Problem

As a result of intensive investigations in order to solve the above problems, the present inventors have found the followings that led to the completion of the present invention: i.e., a compound having a specific structure that contains either one of titanium or zirconium bonded to boron or phosphorus via an oxygen atom and also has a residue of an aliphatic carboxylic acid becomes an adhesion promoter capable of exerting a high adhesive force between rubber and a metal, rather than a cobalt-containing adhesion promoter, without containing cobalt that is associated with toxicity concerns; and the compound also becomes an adhesion promoter capable of exhibiting a high adhesive force between rubber and a metal, as compared with the one positively having an aromatic carboxylic acid residue as disclosed in the aforementioned Patent Document 1.

That is, the present invention includes the following aspects.

[1] A rubber-metal adhesion promoter characterized by including a compound (1) represented by the following general formula (A):

[Chemical Formula 1]

$$[(RCOO)_3MO]_3Z \qquad (A)$$

(in the formula, Z represents a structure selected from the following formulae (z-1) to (z-4);

[Chemical Formula 2]

(z-1)

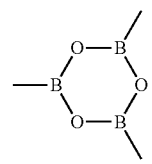
(z-2)

(z-3)

M represents titanium or zirconium; and (RCOO) represents a residue of an aliphatic carboxylic acid having 2 to 25 carbon atoms) is provided.

[2] The rubber-metal adhesion promoter according to the above [1], wherein the aforementioned M is titanium.

[3] The rubber-metal adhesion promoter according to the above [1] or [2], wherein the aforementioned Z is a structure represented by the aforementioned formula (z-1).

[4] The rubber-metal adhesion promoter according to the above [1], wherein the aforementioned (RCOO) is a residue of a saturated aliphatic monocarboxylic acid having 2 to 20 carbon atoms.

[5] The rubber-metal adhesion promoter according to the above [3], wherein the aforementioned (RCOO) is a residue of 2-ethylhexanoic acid, a residue of neodecanoic acid, a residue of hexadecanoic acid or a residue of octadecanoic acid.

[6] The rubber-metal adhesion promoter according to any one of the above [1] to [5], which is used for adhering rubber and a steel cord.

[7] A rubber composition characterized by including: the rubber-metal adhesion promoter according to any one of the above [1] to [6]; and a rubber component.

[8] The rubber composition according to the above [7], which contains 1 to 7 parts by mass of the aforementioned rubber-metal adhesion promoter with respect to 100 parts by mass of the aforementioned rubber component.

[9] A tire characterized by having a steel cord/rubber composite including the rubber composition according to the above [7] or [8] and a steel cord.

Advantageous Effects of Invention

The rubber-metal adhesion promoter of the present invention is, despite being a non-cobalt based promoter, capable of exerting a higher adhesive force between rubber and a metal than a cobalt-containing adhesion promoter, especially even under wet heat conditions. By using the adhesion promoter of the present invention, it is possible to easily obtain a rubber composition capable of suitably producing automobile tires, belt conveyors and the like exhibiting strong adhesion between the steel cord and the rubber.

DESCRIPTION OF EMBODIMENTS

A rubber-metal adhesion promoter of the present invention is characterized by containing a compound (1) as described above. The metal species in the compound (1) is titanium or zirconium. Among them, titanium is preferable, since an adhesion promoter capable of achieving favorable adhesion between the steel cord and the rubber is obtained.

Next, the compound (1) in the present invention will be described in detail. (RCOO) in the compound (1) represents a residue of an aliphatic carboxylic acid having 2 to 25 carbon atoms. The residue of an aliphatic carboxylic acid having less than 2 carbon atoms is unlikely to become an adhesion promoter excellent in compatibility with the rubber, and as a result, it becomes difficult to obtain an adhesion promoter that exerts high adhesive force between the rubber and the metal, and is therefore not preferable. In addition, not only it is difficult to synthesize the compound (1) with the residue of a carboxylic acid having more than 25 carbon atoms, but also it is difficult to disperse in the rubber or adsorb to the surface of the steel cord. As a result, it becomes difficult to obtain an adhesion promoter that exerts high adhesive force between the rubber and the metal, and is therefore not preferable.

As the residue of the aliphatic carboxylic acid having 2 to 25 carbon atoms, for example, residues of an aliphatic monocarboxylic acid or aliphatic dicarboxylic acid can be preferably exemplified. As these residues, for example, residues derived from an aliphatic monocarboxylic acid or aliphatic dicarboxylic acid described below can be preferably exemplified. Here, in the present invention, the number of carbon atoms of the aliphatic carboxylic acid refers to the number of carbon atoms including those of the carboxyl group.

Examples of the aliphatic carboxylic acid having 2 to 25 carbon atoms include saturated aliphatic monocarboxylic acids and unsaturated aliphatic monocarboxylic acids. Examples of the saturated aliphatic monocarboxylic acid include ethanoic acid, propanoic acid, butanoic acid, pentanoic acid, hexanoic acid, 2-ethylhexanoic acid, heptanoic acid, octanoic acid, nonanoic acid, isononanoic acid, decanoic acid, neodecanoic acid, dodecanoic acid, tetradecanoic acid, hexadecanoic acid, heptadecanoic acid, octadecanoic acid, eicosanoic acid, docosanoic acid, tetracosanoic acid and naphthenic acid.

Examples of the unsaturated aliphatic monocarboxylic acid include 9-hexadecenoic acid, cis-9-octadecenoic acid, 11-octadecenoic acid, cis, cis-9,12-octadecadienoic acid, 9,12,15-octadecatrienoic acid, 6,9,12-octadecatrienoic acid, 9,11,13-octadecatrienoic acid, eicosanoic acid, 8,11-eicosadienoic acid, 5,8,11-eicosatrienoic acid, 5,8,11,14-eicosatetraenoic acid, tung oil acid, linseed oil acid, soybean oil acid, resin acid, tall oil fatty acid, rosin acid, abietic acid, neoabietic acid, palustric acid, pimaric acid and dehydroabietic acid.

Examples of the aliphatic dicarboxylic acid having 2 to 25 carbon atoms include saturated aliphatic dicarboxylic acids and unsaturated aliphatic dicarboxylic acids. Examples of the saturated aliphatic dicarboxylic acid include oxalic acid, malonic acid, succinic acid, glutaric acid and adipic acid. Examples of the unsaturated aliphatic dicarboxylic acid include fumaric acid and maleic acid.

Among the aforementioned carboxylic acid residues, residues of saturated aliphatic monocarboxylic acids are preferable because they hardly affect adversely the sulfur crosslinking of the rubber, and as a result, a rubber cured product having less adverse effects on the rubber physical properties which is used for automobile tires, belt conveyors and the like can be obtained. Among residues of saturated fatty acids, a residue of a saturated aliphatic monocarboxylic acid having 2 to 20 carbon atoms is preferable, and a residue of 2-ethylhexanoic acid, a residue of neodecanoic acid, a residue of hexadecanoic acid or a residue of octadecanoic acid is more preferable.

Z in the compound represented by the aforementioned general formula (A) is a structure selected from the following formulae (z-1) to (z-4).

[Chemical Formula 3]

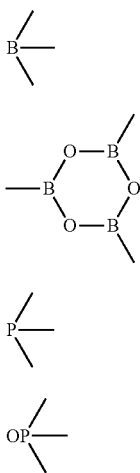

Among the above structures, the structure represented by the above formula (z-1) is preferable because it is easy to obtain an adhesion promoter that exerts high adhesive force between the rubber and the metal.

The compound (1) in the present invention can be obtained, for example, by the following method.

Production Method 1: A method of mixing and heating an aliphatic carboxylic acid (a) having 2 to 25 carbon atoms; an oxide (b-1) of a metal (titanium or zirconium), a hydroxide (b-2) of a metal (titanium or zirconium) or a carbonate (b-3) of a metal (titanium or zirconium) as a metal source; a boric acid ester (d-1) of a lower alcohol having 1 to 5 carbon atoms, a metaboric acid ester (d-2) of a lower alcohol having 1 to 5 carbon atoms, a phosphoric acid ester (d-3) of a lower alcohol having 1 to 5 carbon atoms or a phosphite ester (d-4) of a lower alcohol having 1 to 5 carbon atoms; and an acid (e) capable of forming a volatile ester with a lower alcohol residue of 1 to 5 carbon atoms present in the esters (d-1) to (d-4), and removing the resulting volatile ester.

Production Method 2: A production method including a first step of reacting an aliphatic carboxylic acid (a) having 2 to 25 carbon atoms, an acid (e) capable of forming a volatile ester with a lower alcohol residue present in the ester (d) used in a second step described below and sodium hydroxide in the presence of water to obtain a sodium salt of an aliphatic carboxylic acid and then mixing and heating the sodium salt of the aliphatic carboxylic acid with a sulfate (c-1) of a metal (titanium or zirconium), a chloride (c-2) of a metal (titanium or zirconium) or a nitrate (c-3) of a metal (titanium or zirconium) to obtain a reaction product; followed by a second step of adding, after removing water from the reaction system containing the reaction product, the boric acid ester (d-1) of a lower alcohol, the metaboric acid ester (d-2) of a lower alcohol, the phosphoric acid ester (d-3) of a lower alcohol or the phosphite ester (d-4) of a lower alcohol to the reaction system from which the water has been removed, and allowing the reaction product to react with the esters (d-1) to (d-4).

Examples of the aliphatic carboxylic acid (a) having 2 to 25 carbon atoms include the aforementioned aliphatic monocarboxylic acids having 2 to 25 carbon atoms and the like.

Examples of the oxide (b-1) of the metal (titanium or zirconium) include titanium(IV) oxide and zirconium(IV) oxide. Examples of the hydroxide (b-2) of the metal (titanium or zirconium) include titanium(IV) hydroxide and zirconium(II) hydroxide. Examples of the carbonate (b-3) of the metal (titanium or zirconium) include titanium(IV) carbonate and zirconium(IV) carbonate.

Examples of the sulfate (c-1) of the metal (titanium or zirconium) used in the above Production Method 2 include titanium(IV) sulfate and zirconium(IV) sulfate. Examples of the chloride (c-2) of the metal (titanium or zirconium) include titanium(III) chloride, titanium(IV) chloride and titanium oxychloride. Examples of the nitrate (c-3) of the metal (titanium or zirconium) include titanium(IV) nitrate, zirconium(IV) nitrate and zirconium oxynitrate.

Examples of the boric acid ester (d-1) of a lower alcohol include trimethyl borate, triethyl borate, tripropyl borate and tributyl borate. Examples of the metaboric acid ester (d-2) of a lower alcohol include trimethyl metaborate, triethyl metaborate, tripropyl metaborate and tributyl metaborate. Examples of the phosphoric acid ester (d-3) of a lower alcohol include methyl phosphate, ethyl phosphate, propyl phosphate and butyl phosphate. Examples of the phosphite ester (d-4) of a lower alcohol include methyl phosphite, ethyl phosphite, propyl phosphite and butyl phosphite.

Examples of the acid (e) include ethanoic acid, propanoic acid and butanoic acid.

In the above Production Method 1, the proportion of the compounds (b-1) to (b-3) used as the metal sources is, for example, from 20 to 300 parts by mass per 100 parts by mass of the aliphatic carboxylic acid (a) having 2 to 25 carbon atoms. In addition, the proportion of the esters (d-1) to (d-4) used is, for example, from 10 to 50 parts by mass per 100 parts by mass of the aliphatic carboxylic acid (a) having 2 to 25 carbon atoms. Further, the proportion of the acid (e) used is, for example, from 10 to 50 parts by mass per 100 parts by mass of the aliphatic carboxylic acid (a) having 2 to 25 carbon atoms.

In the above Production Method 2, the proportion of the compounds (c-1) to (c-3) used as the metal sources is, for example, from 20 to 800 parts by mass per 100 parts by mass of the aliphatic carboxylic acid (a) having 2 to 25 carbon atoms. In addition, the proportion of the esters (d-1) to (d-4) used is, for example, from 10 to 50 parts by mass per 100 parts by mass of the aliphatic carboxylic acid (a) having 2 to 25 carbon atoms. Further, the proportion of the acid (e) used is, for example, from 10 to 50 parts by mass per 100 parts by mass of the aliphatic carboxylic acid (a) having 2 to 25 carbon atoms.

Among the above production methods, the Production Method 1 is preferable, and in particular, the production method including a first step of mixing and heating an aliphatic carboxylic acid (a) having 2 to 25 carbon atoms, an acid (e) capable of forming a volatile ester with a lower alcohol residue of 1 to 5 carbon atoms present in the esters (d-1) to (d-4), and the compounds (b-1) to (b-3) as the metal sources to obtain a reaction product; followed by a second step of adding, after removing water from the reaction system containing the reaction product, the esters (d-1) to (d-4) to the reaction system from which the water has been removed, and allowing the reaction product to react with the esters (d-1) to (d-4), is preferable because it is possible to prevent the hydrolysis of the esters (d-1) to (d-4) by the water produced in the first step, and as a result, it is possible to efficiently produce the compound (1) in the present invention.

In the above Production Method 1, the temperature for reacting the aliphatic carboxylic acid (a) having 2 to 25 carbon atoms, the compounds (b-1) to (b-3) as the metal sources, the esters (d-1) to (d-4) and the acid (e) is, for example, from 100 to 250° C., and preferably from 150 to 220° C. In addition, the reaction time is, for example, from 1 to 20 hours, and preferably from 1 to 5 hours.

In the above Production Method 2, the reaction temperature at the time of reacting the aliphatic carboxylic acid (a) having 2 to 25 carbon atoms with sodium hydroxide in the presence of an organic solvent is usually from 20 to 100° C. In addition, the reaction time is usually from 1 to 5 hours.

In the above Production Method 2, the reaction temperature at the time of reacting the sodium salt of an aliphatic carboxylic acid with the compounds (c-1) to (c-3) is usually from 20 to 100° C. In addition, the reaction time is usually from 1 to 5 hours.

In the Production Method 2, after reacting the sodium salt of the aliphatic carboxylic acid with the compounds (c-1) to (c-3), an aqueous layer in the reaction system is separated. Thereafter, by removing the solvent present in the oil layer by distillation under reduced pressure, the rubber-metal adhesion promoter (fatty acid metal salt) of the present invention can be obtained.

The rubber composition of the present invention is characterized by containing the adhesion promoter of the present invention and a rubber component. As the rubber component, for example, diene-based rubber can be used. Examples of the diene-based rubber include natural rubber (NR) and diene-based synthetic rubber. Examples of the diene-based synthetic rubber include isoprene rubber (IR), butadiene rubber (BR), styrene butadiene rubber (SBR), styrene isoprene butadiene rubber (STBR), ethylene propylene diene rubber (EPDM), chloroprene rubber (CR) and acrylonitrile butadiene rubber (NBR). Among these rubber components, NR which is easy to elongate and crystallize and excellent in fracture properties is preferable.

In the rubber composition according to the present invention, a filler such as carbon black or silica can be blended as a reinforcing agent.

The carbon black is not particularly limited, and for example, carbon black of SAF, ISAF, HAF or FEF type can be used, and two or more types of these may be used in combination. The amount of the carbon black added is not particularly limited, but it is preferably from 20 to 100 parts by mass, and more preferably from 40 to 80 parts by mass with respect to 100 parts by mass of the diene-based rubber.

Examples of the silica include wet silica (hydrous silicic acid), dry silica (anhydrous silicic acid) and surface treated silica. In the case of adding silica, the added amount thereof is not particularly limited, but it is preferably 0 parts by mass or more and 40 parts by mass or less, and more preferably 0.1 parts by mass or more and 20 parts by mass or less, with respect to 100 parts by mass of the diene-based rubber.

Sulfur as a vulcanizing agent is usually added to the rubber composition according to the present invention. The added amount of sulfur is preferably from 1 to 10 parts by mass, and more preferably from 2 to 8 parts by mass with respect to 100 parts by mass of the diene-based rubber. Examples of sulfur include powdered sulfur, precipitated sulfur, colloidal sulfur, insoluble sulfur and oil-treated sulfur, and are not particularly limited.

A vulcanization accelerator can be added to the rubber composition of the present invention. As the vulcanization accelerator, for example, a sulfenamide-based vulcanization accelerator can be mentioned. Here, examples of the sulfenamide vulcanization accelerator include N-cyclohexyl-2-benzothiazole sulfenamide (CZ, JIS abbreviation: CBS), N-tert-butyl-2-benzothiazole sulfenamide (NS, JIS Abbreviation: BBS), N-oxydiethylene-2-benzothiazole sulfenamide (OBS), N,N-diisopropyl-2-benzothiazole sulfenamide (DPBS) and N,N-dicyclohexyl-2-benzothiazole sulfenamide (DZ, JIS abbreviation: DCBS).

The content of the vulcanization accelerator is preferably from 1 to 12 parts by mass, more preferably from 2 to 10 parts by mass, and even more preferably from 3 to 9 parts by mass, with respect to 100 parts by mass of the rubber component.

In addition to the above components, various compounding agents can be arbitrarily added to the rubber composition according to the present invention. Examples of such compounding agents include stearic acid, wax, oil, antioxidants and processing aids.

The rubber composition of the present invention can be prepared by kneading using a mixer such as a Banbury mixer or a kneader that is commonly used.

The rubber composition of the present invention can be suitably used, in particular, as a rubber composition for covering various steel cords. In particular, it is preferably used as a rubber composition for covering (topping) a steel cord used as a reinforcing material for a pneumatic tire such as a belt layer, a carcass layer, a chafer layer and the like, and a steel cord topping sheet is produced by a topping device such as a steel calender in accordance with a conventional method and this is used as a tire reinforcing member and molded and vulcanized in accordance with a conventional method, whereby a tire having a steel cord/rubber composite can be produced.

The content of the rubber-metal adhesion promoter according to the present invention in the rubber composition of the present invention is preferably from 1 to 10.0 parts by mass, and more preferably from 1 to 7.0 parts by mass, with respect to 100 parts by mass of the rubber component.

EXAMPLES

Hereinafter, the present invention will be described in detail by referring to Examples of the present invention and comparing them with Comparative Examples. In the Examples and Comparative Examples, unless stated otherwise, "parts" and "%" refer to mass-referenced values.

Synthesis Example 1

Synthesis of Compound (1-1)

796 g of a 20% NaOH aqueous solution was added to a mixed acid of 63 g of acetic acid and 513 g of neodecanoic acid, and then the resulting mixture was heated and stirred at 90° C. for 1 hour. Thereafter, 800 g of a 30% titanium sulfate solution was charged thereto, and then the resulting mixture was heated and stirred at 90° C. for 1 hour, and dried under reduced pressure at 150° C. for 1 hour. Then, 80 g of tributyl borate was allowed to react with the produced metal salt of titanium, and butyl acetate produced as a by-product was distilled off to obtain a compound (1-1) used in the present invention. It should be noted that the compound (1-1) can also be said to be an adhesion promoter (1-1) of the present invention containing the compound (1-1).

Synthesis Example 2

Synthesis of Compound (1-2)

796 g of a 20% NaOH aqueous solution was added to a mixed acid of 63 g of acetic acid and 513 g of neodecanoic acid, and then the resulting mixture was heated and stirred at 90° C. for 1 hour. Thereafter, 322 g of zirconium(IV)

oxychloride octahydrate was charged thereto, and then the resulting mixture was heated and stirred at 90° C. for 1 hour, and dried under reduced pressure at 150° C. for 1 hour. Then, 80 g of tributyl borate was allowed to react with the produced metal salt of zirconium, and butyl acetate produced as a by-product was distilled off to obtain a compound (1-2) used in the present invention. It should be noted that the compound (1-2) can also be said to be an adhesion promoter (1-2) of the present invention containing the compound (1-2).

Comparative Synthesis Example 1

Synthesis of Comparative Compound (1'-1)

210 g of neodecanoic acid, 147 g of propionic acid and 300 g of xylene were charged into a reaction flask and heated to 50° C. with mechanical stirring. 171 g of cobalt(II) hydroxide was added thereto, and the temperature was raised to 90° C. with mechanical stirring to produce a mobile blue liquid. Further, heat was applied and the reaction water was removed by xylene loading using a Dean & Stark trap. After the temperature reached 140° C., 73 g of benzoic acid dissolved in 150 g of xylene was gradually added to the reaction mixture, and the produced water was continuously removed.

After completion of the water removal, xylene was removed by short path distillation to a maximum temperature of 155° C., and a vacuum was applied to complete the removal. 138 g of tributyl borate was added thereto. The reaction mixture was heated to 190° C. and refluxed for 3 hours. 220 g of n-butyl propionate was then removed by distillation at the maximum temperature of 220° C., and a vacuum was applied to complete the ester removal to obtain a comparative compound (1'-1).

The comparative compound (1'-1) was a hard blue solid represented by the following formula:

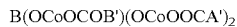

[In the formula, OCOA' is a neodecanoic acid ester, and OCOB' is a benzoic acid ester]. It should be noted that the comparative compound (1'-1) can also be said to be a comparative adhesion promoter (1'-1) containing the comparative compound (1'-1).

Example 1

Preparation of Rubber Composition of the Present Invention 100 parts of natural rubber (grade: RSS 1), 4 parts of the adhesion promoter (1-1), 50 parts of carbon black (SEAST G-S manufactured by Tokai Carbon Co., Ltd.), 5 parts of oil (Dutrex R manufactured by Shell Chemicals Japan Ltd.), 8 parts of zinc white, 1 part of an antioxidant (Nocrac 810NA manufactured by Ouchi Shinko Chemical Industrial Co., Ltd.), 5 parts of insoluble sulfur, 2 parts of stearic acid and 0.5 parts of a vulcanization accelerator (Nocceler CZ, manufactured by Ouchi Shinko Chemical Industrial Co., Ltd.) were kneaded at 40° C. to obtain a rubber composition (1) of the present invention. A cured product (test piece) of a rubber composition in which a steel cord was sandwiched was prepared using the obtained rubber composition (1), and the adhesive properties between the steel cord and rubber were evaluated. The method for preparing a test piece and the method for evaluating the adhesive properties are shown below. In addition, the evaluation results are shown in Table 1.

<Method for Preparing Test Piece>

The rubber composition (1) was subjected to a heat treatment by a double test roller to prepare a rubber sheet having a width of 100 mm, a thickness of 6 mm and a length of 100 mm. Two rubber pieces having a width of 10 mm, a thickness of 6 mm and a length of 60 mm were cut out from the rubber sheet. A 1×4×0.25 mm steel cord plated with brass (Cu 65%, Zn 35%) was sandwiched between the aforementioned two rubber pieces and vulcanized at 160° C. for 10 minutes to prepare a rubber composition test piece to which the steel cord was adhered.

<Evaluation Method of Adhesive Properties>

A pulling test was conducted by a method in accordance with ASTM D2229 using the aforementioned test piece, and the adhesive force between the rubber and the steel cord was measured. For the measurement of the adhesive force, the following three types of measurements were carried out.

Initial adhesive force: A test piece was prepared by vulcanization under the above vulcanization conditions, and was subjected to the measurement immediately afterwards.

Adhesive force after hygrothermal aging test: The test piece vulcanized under the above vulcanization conditions was subjected to water immersion aging by being immersed in hot water at 90° C. for 72 hours, and then the adhesive force was measured.

Adhesive force after heat aging test: The test piece vulcanized under the above vulcanization conditions was left to stand at 110° C. for 72 hours to measure the adhesive force.

It should be noted that the measured values of the above three adhesive forces are relative adhesive force values when the adhesive forces of a comparative metal salt (1'-2) described later are taken as 100.

Example 2

A rubber composition (2) was obtained in the same manner as in Example 1 except that the compound (1-2) [adhesion promoter of the present invention] was used. An evaluation test of adhesive properties was carried out in the same manner as in Example 1, and the results are shown in Table 1. It should be noted that the amount of the compound (1-2) used was such that the metal molar concentration in the rubber composition was the same.

TABLE 1

| | Metal Salt (1) or Compound (2) [Adhesion Promoter] | | | | | Adhesion after aging test | |
|---|---|---|---|---|---|---|---|
| | Compound | Synthesis Example | Compound name | Amount used (parts) | Initial Adhesion | Adhesion after hygrothermal aging test | Adhesion after heat aging test |
| Ex. 1 | (1-1) | Synthesis Example 1 | Titanium(IV) boron neodecanoate | 4.0 | 110 | 105 | 120 |
| Ex. 2 | (1-2) | Synthesis Example 2 | Zirconium(IV) boron neodecanoate | 4.6 | 108 | 110 | 113 |

Comparative Examples 1, 2 and 3

Preparation of Comparative Rubber Compositions

Comparative rubber compositions (1'), (2') and (3') were obtained in the same manner as in Example 1 except that the compound (1'-1) and the metal salts (1'-2) to (1'-3) [comparative adhesion promoters] shown in Table 2 were used. An evaluation test of adhesive properties was carried out in the same manner as in Example 1, and the results are shown in Table 2. It should be noted that in Comparative Examples 1, 2 and 3, the amount of each of the compound (1'-1) and the metal salts (1'-2) to (1'-3) used was such that the metal molar concentration in the rubber composition was the same.

TABLE 2

| | Metal Salt (1') or Compound (2') [Adhesion Promoter] | | | | | Adhesion after aging test | |
|---|---|---|---|---|---|---|---|
| | Metal Salt or Compound | Synthesis Example | Metal salt name or compound name | Amount used (parts) | Initial Adhesion | Adhesion after hygrothermal aging test | Adhesion after heat aging test |
| Comp. Ex. 1 | (1'-1) | Comparative Synthesis Example 1 | Cobalt(II) boron (neodecanoate + benzoate) | 3.3 | 75 | 80 | 80 |
| Comp. Ex. 2 | (1'-2) | | Cobalt(II) 2-ethylhexanoate | 2.7 | 100 | 100 | 100 |
| Comp. Ex. 3 | (1'-3) | | Cobalt(II) boron neodecanoate | 1.9 | 100 | 102 | 101 |

INDUSTRIAL APPLICABILITY

The present invention is used, for example, in automobile tires, belt conveyors and the like in order to promote adhesion between rubber and a metal to enhance the performance.

The invention claimed is:

1. A rubber-metal adhesion promoter comprising a compound (1) represented by the following general formula (A):

[(RCOO)$_3$MO]$_3$Z     (A)

wherein Z represents a structure selected from the following formulae (z-1) to (z-4);

(z-1)

(z-2)

(z-3)

(z-4)

M represents titanium; and (RCOO) represents a residue of an aliphatic carboxylic acid having 2 to 25 carbon atoms.

2. The rubber-metal adhesion promoter according to claim 1, wherein said Z is a structure represented by said formula (z-1).

3. The rubber-metal adhesion promoter according to claim 2, wherein said (RCOO) is a residue of 2-ethylhexanoic acid, a residue of neodecanoic acid, a residue of hexadecanoic acid or a residue of octadecanoic acid.

4. A rubber composition comprising:
the rubber-metal adhesion promoter according to claim 3; and
a rubber component.

5. A rubber composition comprising:
the rubber-metal adhesion promoter according to claim 2; and
a rubber component.

6. The rubber composition according to claim 5, which contains 1 to 7 parts by mass of said rubber-metal adhesion promoter with respect to 100 parts by mass of said rubber component.

7. A tire comprising a steel cord/rubber composite including the rubber composition according to claim 5 and a steel cord.

8. The rubber-metal adhesion promoter according to claim 1, wherein said (RCOO) is a residue of a saturated aliphatic monocarboxylic acid having 2 to 20 carbon atoms.

9. A rubber composition comprising:
the rubber-metal adhesion promoter according to claim 8; and
a rubber component.

10. The rubber composition according to claim 9, which contains 1 to 7 parts by mass of said rubber-metal adhesion promoter with respect to 100 parts by mass of said rubber component.

11. A tire comprising a steel cord/rubber composite including the rubber composition according to claim 9 and a steel cord.

12. The rubber-metal adhesion promoter according to claim 1, which is used for adhering rubber and a steel cord.

13. A rubber composition comprising:
the rubber-metal adhesion promoter according to claim 12; and
a rubber component.

14. A rubber composition comprising:
the rubber-metal adhesion promoter according to claim 1; and
a rubber component.

15. The rubber composition according to claim 14, which contains 1 to 7 parts by mass of said rubber-metal adhesion promoter with respect to 100 parts by mass of said rubber component.

16. A tire comprising a steel cord/rubber composite including the rubber composition according to claim 14 and a steel cord.

* * * * *